United States Patent
Kondou et al.

(10) Patent No.: US 9,476,891 B2
(45) Date of Patent: Oct. 25, 2016

(54) INSULIN ASSAY

(75) Inventors: Junichi Kondou, Ryugasaki (JP);
Tomo Shimizu, Ryugasaki (JP);
Mitsuaki Yamamoto, Ryugasaki (JP);
Yasushi Nakamura, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 534 days.

(21) Appl. No.: 13/122,930

(22) PCT Filed: Jul. 21, 2010

(86) PCT No.: PCT/JP2010/062261
§ 371 (c)(1),
(2), (4) Date: Apr. 6, 2011

(87) PCT Pub. No.: WO2011/010673
PCT Pub. Date: Jan. 27, 2011

(65) Prior Publication Data
US 2011/0195438 A1    Aug. 11, 2011

(30) Foreign Application Priority Data
Jul. 21, 2009 (JP) ................. 2009-170292

(51) Int. Cl.
*G01N 33/74* (2006.01)
*C07K 16/26* (2006.01)
*G01N 33/53* (2006.01)

(52) U.S. Cl.
CPC .............. *G01N 33/74* (2013.01); *C07K 16/26* (2013.01); *G01N 33/53* (2013.01); *G01N 2333/62* (2013.01)

(58) Field of Classification Search
None
See application file for complete search history.

(56) References Cited

U.S. PATENT DOCUMENTS

| 4,514,505 | A | * | 4/1985 | Canfield et al. | 436/500 |
| 5,070,025 | A | * | 12/1991 | Klein et al. | 436/546 |
| 5,561,049 | A | | 10/1996 | Vold et al. | |
| 5,583,003 | A | * | 12/1996 | Hillyard et al. | 435/7.25 |
| 5,985,579 | A | * | 11/1999 | Buechler et al. | 435/7.1 |
| 7,338,813 | B2 | * | 3/2008 | Obana | C08F 212/08 428/403 |
| 7,749,712 | B2 | | 7/2010 | Pulli et al. | |
| 2006/0246506 | A1 | | 11/2006 | Pulli et al. | |
| 2009/0175840 | A1 | * | 7/2009 | Kashyap et al. | 424/94.4 |
| 2011/0165701 | A1 | * | 7/2011 | Takahashi et al. | 436/501 |

FOREIGN PATENT DOCUMENTS

| DE | 36 36 724 A1 | 6/1988 |
| EP | 0 314 338 A1 | 5/1989 |
| JP | 1-98968 A | 4/1989 |
| JP | 3-118472 A | 5/1991 |
| JP | 5-297000 A | 11/1993 |
| JP | 9-5115852 A | 11/1997 |
| JP | 2006-506634 A | 2/2006 |
| JP | 2007-171213 A | 7/2007 |
| WO | WO 2010/026758 A1 * | 3/2010 | ............. C07K 16/42 |

OTHER PUBLICATIONS

Lindstrom et al. "Use of a Novel Double-Antibody Technique to Describe the Pharmacokinetics of Rapid-Acting Insulin Analogs" Diabetes Care 25:1049-1054, 2002.*
Marcovina et al. Standardization of Insulin Immunoassays: Report of the American Diabetes Association Workgroup Clinical Chemistry 2007, 53:4711-716.*
Sapin et al. "Elecsys Insulin Assay: Free Insulin Determination and the Absence of Cross-Reactivity with Insulin Lispro" Clinical Chemistry Mar. 2001 vol. 47 No. 3 602-605.*
Marcovina et al., accompanying online Supplemental Information for the article "Standardization of Insulin Immunoassays" (2007), retrieved from http://www.clinchem.org/content/suppl/2008/03/17/clinchem.2006.082214.DC1/Material_and_Methods.pdf (eight pages).*
Harlow, E. and Lane, D., Antibodies: A Laboratory Manual (1988) Cold Spring Harbor Laboratory Press, Cold Spring Harbor, NY, p. 141.*
Sapin et al. "Insulin assays: previously known and new analytical features" Clin Lab. 2003;49(3-4):113-21.*
Allauzen et al. "Immunoanalysis of human insulin using monoclonal antibodies reveals antigenicity of evolutionarily conserved residues" Mol Immunol. Jan. 1995;32(1):27-36.*
Allauzen et al., "Epitope mapping and binding analysis of insulin-specific monoclonal antibodies using biosensor approach," Journal of Immunological Methods (1995), vol. 182, pp. 27-32.
Extended European Search Report issued Dec. 4, 2012, in European Patent Applicaton No. 10802293.0.
Rathjen. D. A. and P. A. Underwood, "Identification of antigenic determinants of insulin recognize by monoclonal antibodies," Molecular Immunology (1986), vol. 23, No. 4, pp. 441-450.
Winter et al., "Increased production of human proinsulin in the periplasmic space of *Escherichia coil* by fusion to DsbA," Journal of Biotechnology (2000), vol. 84, pp. 175-185.
International Search Report issued Nov. 2, 2010, in PCT International Application No. PCT/JP2010/062261.
Ishijima et al., Japanese Journal of Clinical Laboratory Automation, Aug. 1, 2000, vol. 25, No. 4, p. 579.
English translation of International Preliminary Report on Patentability and Written Opinion issued Mar. 22, 2012, in PCT International Application No. PCT/JP2010/062261.

* cited by examiner

*Primary Examiner* — Christine Foster
(74) *Attorney, Agent, or Firm* — Birch, Stewart, Kolasch & Birch, LLP

(57) ABSTRACT

The present invention provides an insulin-specific assay and an assay reagent capable of sensitively and specifically assaying insulin using an antibody having a property of reacting with insulin bound to an anti-insulin antibody while not reacting with insulin not bound to an anti-insulin antibody, without being affected by proinsulin and insulin analogs.

4 Claims, 9 Drawing Sheets

FIG. 4-1
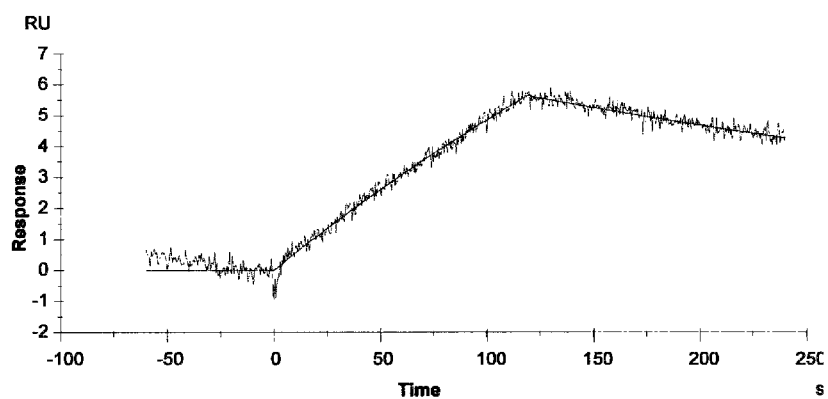
(a) 66221-ANTIBODY–PROINSULIN
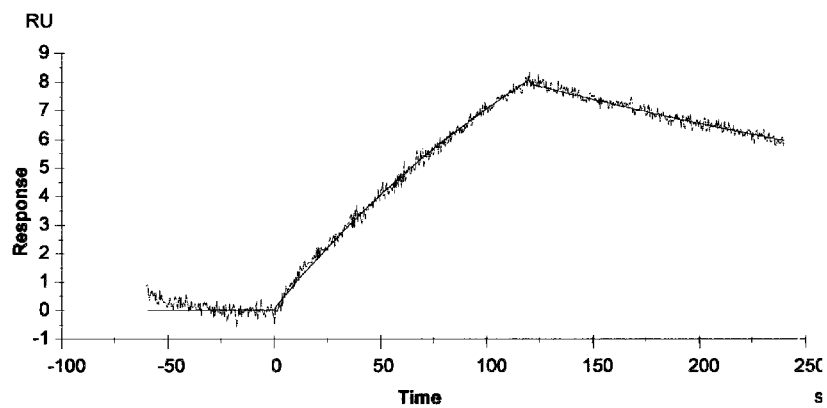
(b) 66221-ANTIBODY–INSULIN LISPRO
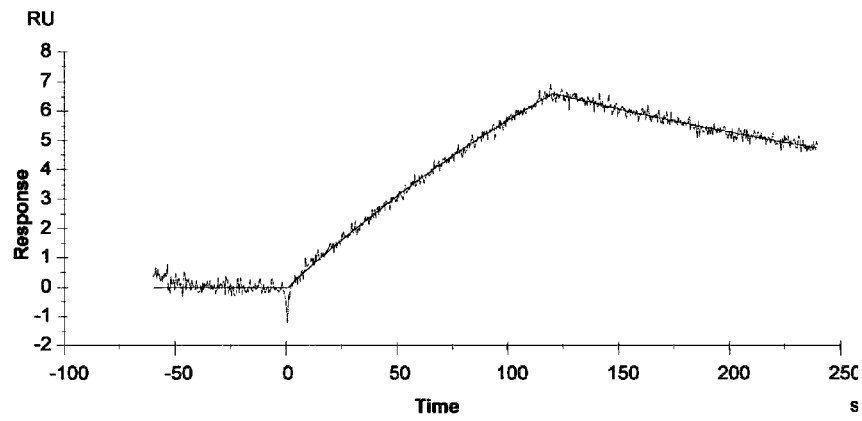
(c) 66221-ANTIBODY–INSULIN ASPART FIG. 5-1
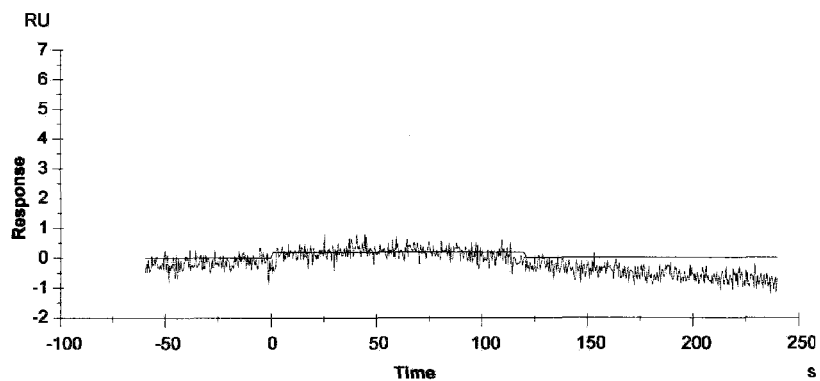
(a) 66226-ANTIBODY–PROINSULIN
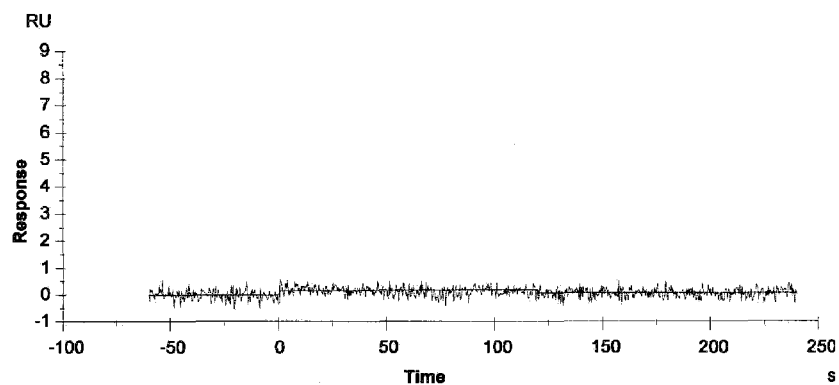
(b) 66226-ANTIBODY–INSULIN LISPRO
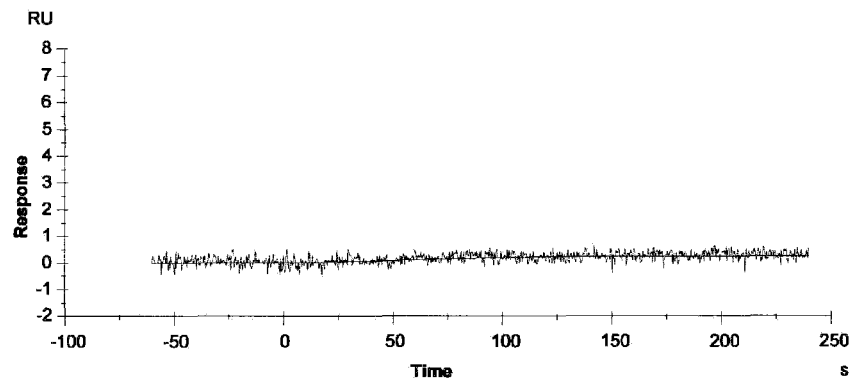
(c) 66226-ANTIBODY–INSULIN ASPART (d) 66226-ANTIBODY–INSULIN GLARGINE (e) 66226-ANTIBODY–INSULIN DETEMIR

INSULIN ASSAY

TECHNICAL FIELD

The present invention relates to an insulin assay and insulin assay reagent utilizing an immune reaction. In particular, this invention involves an antibody that reacts with insulin bound to another anti-insulin antibody but does not react with insulin not bound to the anti-insulin antibody.

BACKGROUND ART

Insulin is a peptide hormone (molecular weight: approximately 5800) that is produced via a precursor, proinsulin, in the beta cells in the pancreatic islets of Langerhans. Insulin is involved in sugar, amino acid, and fat metabolism, and it is physiologically important in the hypoglycemic effect. Diabetes is caused by insufficient insulin secretion due to decrease in or the functional deterioration of beta cells or due to insufficient insulin action in peripheral tissues. Therefore, the measurement of blood insulin concentration reflecting the insulin secretory function of beta cells is a useful index for the diagnosis and understanding of the clinical condition of diabetes and determination of the cause of abnormal glucose tolerance.

The following techniques are known insulin assays using monoclonal antibodies.

Patent Document 1 discloses a method of quantitating insulin in accordance with an enzyme-linked immunosorbent assay (ELISA). This assay uses a monoclonal antibody bound to an insoluble carrier and a monoclonal antibody not competing with the said antibody for an epitope that is labeled with an enzyme.

Patent Document 2 discloses a method of quantitating insulin in accordance with a particle agglutination immunoassay. This assay uses two monoclonal antibodies that have different recognition sites and are bound to insoluble carriers.

Although both documents disclose methods of assaying insulin using a plurality of monoclonal antibodies that have different recognition sites for insulin, no disclosure is made regarding the cross-reactivity with proinsulin or insulin analogs, such as insulin analog formulations. Therefore, it is not known whether insulin can be measured specifically and sensitively.

PRIOR ART DOCUMENTS

Patent Documents

Patent Document 1: Japanese Laid-Open Patent Publication No. H01-148962
Patent Document 2: Japanese Laid-Open Patent Publication No. H03-118472

SUMMARY OF THE INVENTION

Problem to be Solved by the Invention

The present invention provides an insulin-specific assay and an assay reagent capable of sensitively and specifically assaying insulin without being affected by proinsulin and insulin analogs.

Means for Solving the Problem

As a result of extensive research, the inventors surprisingly discovered that insulin can sensitively and specifically be assayed without being affected by proinsulin and insulin analogs by combining a first monoclonal antibody reactive with insulin with a second monoclonal antibody reactive with insulin bound to the first monoclonal antibody but not with insulin not bound to the first monoclonal antibody. Through further research, the inventors discovered that various forms of this insulin assay can be established using antibodies reactive with insulin bound to anti-insulin antibodies (insulin-anti-insulin antibody complexes, hereinafter, sometimes referred to as "insulin-antibody complex"), thereby completing the present invention. Therefore, the present invention includes the following constituent elements:

[1] An insulin assay using an antibody that reacts with insulin bound to an anti-insulin antibody but does not react with insulin not bound to an anti-insulin antibody.

[2] The insulin assay of [1], using two types of antibodies, wherein
1) a first antibody reacts with insulin, and
2) a second antibody reacts with insulin bound to the first antibody but does not react with insulin not bound to the first antibody.

[3] The insulin assay of [2], wherein both the first and second antibodies are monoclonal antibodies.

[4] The insulin assay of [2], wherein the first antibody is a polyclonal antibody and the second antibody is a monoclonal antibody.

[5] The insulin assay of [3], wherein the first monoclonal antibody consists of two or more monoclonal antibodies having different recognition sites.

[6] The insulin assay of any one of [3] to [5], wherein at least one of the monoclonal antibodies is an antibody that is not reactive with proinsulin or insulin analogs.

[7] The insulin assay of any one of [3] to [6], wherein the second monoclonal antibody is an antibody that is not reactive with proinsulin or insulin analogs.

[8] The insulin assay of any one of [3], [5], [6], and [7], wherein the first and second monoclonal antibodies are immobilized to latex and insulin is assayed by a latex immunoagglutination assay.

[9] The insulin assay of any one of [3], [5], [6], and [7], wherein the first monoclonal antibody is immobilized to a solid phase, the second monoclonal antibody is labeled with a labeling material, and insulin is assayed by ELISA.

[10] The insulin assay of any one of [3], [5], [6], and [7], wherein the first monoclonal antibody is labeled with a labeling material, the second monoclonal antibody is immobilized to a solid phase, and insulin is assayed by ELISA or immunochromatography.

[11] An insulin assay reagent comprising an antibody capable of reacting with insulin bound to an anti-insulin antibody while not reacting with insulin not bound to an anti-insulin antibody.

[12] The insulin assay reagent of [11], comprising two types of antibody, wherein
1) the first antibody has the property of reacting with insulin, and
2) the second antibody has the property of reacting with insulin bound to the first antibody but does not react with insulin not bound to the first antibody.

[13] The insulin assay reagent of [12], wherein both the first and second antibodies are monoclonal antibodies.

[14] The insulin assay reagent of [12], wherein the first antibody is a polyclonal antibody and the second antibody is a monoclonal antibody.

[15] The insulin assay reagent of [13], wherein the first monoclonal antibody consists of two or more monoclonal antibodies having recognition sites different from each other.

[16] The insulin assay reagent of any one of [13] to [15], wherein at least one of the monoclonal antibodies is an antibody that is not reactive with proinsulin or insulin analogs.

[17] The insulin assay reagent of any one of [13] to [16], wherein the second monoclonal antibody is an antibody that is not reactive with proinsulin or insulin analogs.

[18] The insulin assay reagent of any one of [13], [15], [16], and [17], wherein the first and second monoclonal antibodies are immobilized in latex and insulin is assayed by latex immunoagglutination assay.

[19] The insulin assay reagent of any one of [13], [15], [16], and [17], wherein the first monoclonal antibody is immobilized to a solid phase, the second monoclonal antibody is labeled with a labeling material, and insulin is assayed by ELISA.

[20] The insulin assay reagent of any one of [13], [15], [16], and [17], wherein the first monoclonal antibody is labeled with a labeling material, the second monoclonal antibody is immobilized to a solid phase, and insulin is assayed by ELISA or immunochromatography.

[21] A monoclonal antibody having the following properties:
  1) not reacting with insulin that is not bound to an anti-insulin antibody, and
  2) reacting with insulin that is bound to an anti-insulin antibody.

[22] The monoclonal antibody of [21], further having the property of not reacting with proinsulin or insulin analogs.

[23] A method of screening monoclonal antibodies comprising the following steps:
  1) selecting an antibody reactive with insulin, and
  2) selecting a monoclonal antibody reactive with insulin that is bound to the antibody selected in step 1) but is not reactive with insulin that is not bound to the said antibody.

Effect of the Invention

With the present invention, insulin can be sensitively and specifically assayed without being affected by proinsulin and insulin analogs. Since insulin secretion from the beta cells can be accurately monitored by the present invention, the present invention may also be used for providing a picture of the clinical condition of diabetes and would therefore be very useful.

BRIEF DESCRIPTION OF DRAWINGS

In FIG. 1, (a) through (e) are indicative of the variations in the amino acid sequence from various insulin analog formulations in consideration of reactivity with antibodies of the present invention. Alphabetic characters in the circles of FIG. 1 denote amino acids represented by one character. Insulin lispro: (a) and (b) are "K-P" instead of "P-K" (SEQ ID NO:3). Insulin aspart: (a) is "D" instead of "P" at amino acid position 28 (SEQ ID NO:4). Insulin glargine: (d) is "G" instead of "N" at amino acid position 21 (SEQ ID NO:5) and "RR" is added to "T" of (c) (SEQ ID NO:6). Insulin detemir: (c) is not "T" at amino acid position 30 (SEQ ID NO:7) and myristic acid ($C_{14}H_{28}O_2$) is added to "K" of (b). Insulin glulisine: (b) is "E" instead of "K" and (e) is "K" instead of "N" (SEQ ID NO:8).

FIG. 4-1 is a diagram of the results of a test using BIACORE (registered trademark) T100 for examining reactivity of the 66221-antibody with proinsulin and various insulin analog formulations. (a), (b), and (c) are the results for proinsulin, insulin lispro, and insulin aspart, respectively.

FIG. 4-2 is the same as above. (d) and (e) are results for insulin glargine and insulin detemir, respectively.

FIG. 5-1 is a diagram of the results of a test using BIACORE (registered trademark) T100 for examining reactivity of the 66226-antibody with proinsulin and various insulin analog formulations. (a), (b), and (c) are results for proinsulin, insulin lispro, and insulin aspart, respectively.

FIG. 5-2 is the same as above. (d) and (e) are the results for insulin glargine and insulin detemir, respectively.

MODES FOR CARRYING OUT THE INVENTION

Figure 1:
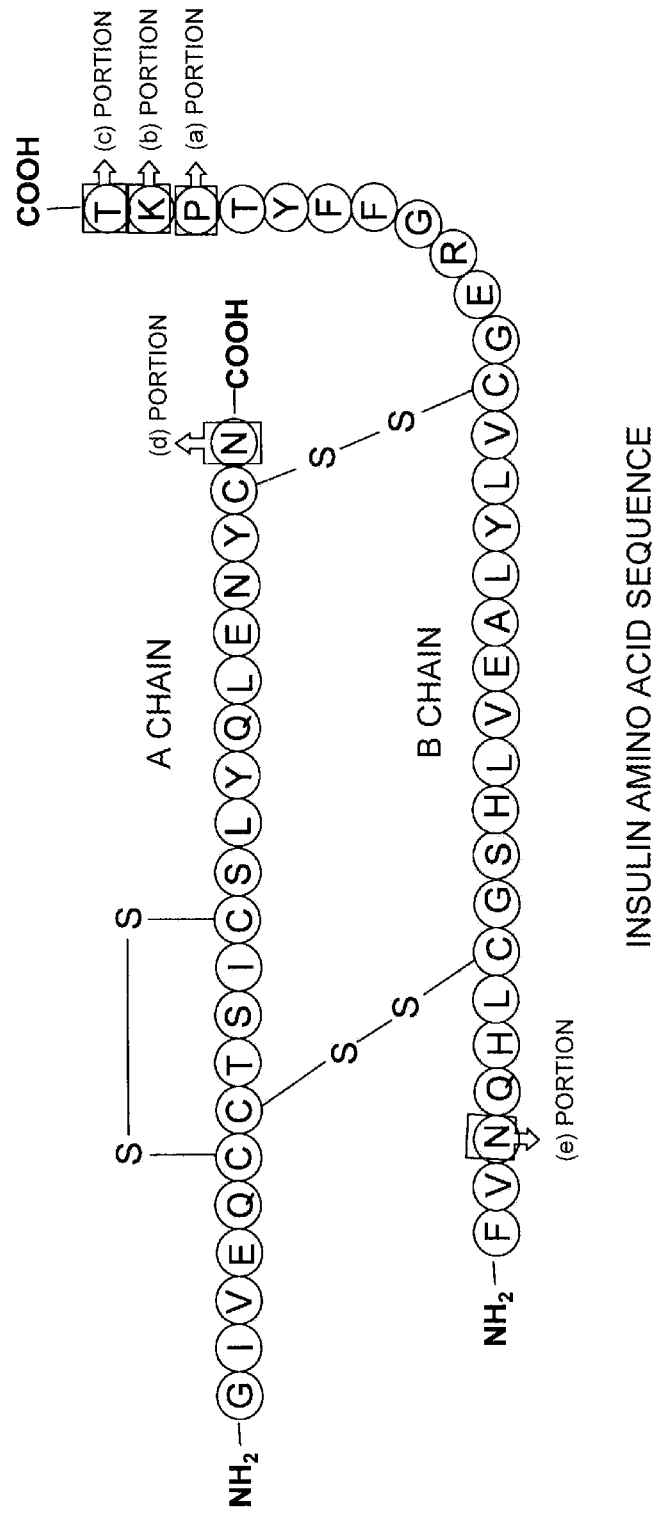
FIG. 1 is a scheme of an amino acid sequence of insulin (SEQ ID NOS: 1 and 2).

Embodiments of the present invention will now be described by considering aspect [3] described below as an example, which is representative of the present invention. Aspect [3] is specifically described as follows: "an insulin assay using two types of monoclonal antibodies, wherein
  (1) the first monoclonal antibody reacts with insulin, and
  (2) the second monoclonal antibody reacts with insulin bound to the first monoclonal antibody and not with insulin not bound to the first monoclonal antibody."

The monoclonal antibodies of the present invention include the first and second monoclonal antibodies, and these antibodies are used in combination for assaying insulin. The first monoclonal antibody may be any monoclonal antibody as long as it is reactive with insulin, and it cannot be only a whole antibody molecule but also a functional fragment that is reactive with insulin, such as the Fab' portion of the antibody.

The second monoclonal antibody may be any monoclonal antibody as long as it has the properties of 1) and 2) as follows:

1) the second monoclonal antibody is not reactive with insulin not bound to the first monoclonal antibody, and 2) the second monoclonal antibody is reactive with insulin bound to the first monoclonal antibody.

If "the second monoclonal antibody reacts with insulin bound to the first monoclonal antibody" as described above, it is desirable that a reaction site (recognition site) of the second monoclonal antibody recognizes a change in the structure of insulin generated by binding to the first monoclonal antibody and reacts with the insulin having the changed structure. In this case, "a change in the structure of insulin" represents a change in the structure generated independently in an insulin molecule itself because of the formation of an insulin-antibody complex or a structure comprising an antibody and insulin molecule cooperatively in insulin bound to the antibody.

Since it is desirable that the assay of the present invention not be affected by proinsulin and insulin analogs, at least one monoclonal antibody is desirably not reactive with proinsulin and insulin analogs. The insulin analogs specifically include insulin analog formulations such as insulin lispro, insulin aspart, insulin glargine, insulin detemir, and insulin glulisine.

One form of the second monoclonal antibody of the present invention may be an antibody that does not cross-react with any of these compounds, and if such an antibody is used in the insulin assay, insulin can be specifically measured even in the presence of the compounds in a sample. If one of the monoclonal antibodies does not react with proinsulin and insulin analogs, the other monoclonal antibody may be reactive or nonreactive with these analogs.

Although the expressions "reacts with" insulin, "recognizing" insulin, "binding to" insulin, and "exhibiting cross-reactivity with/cross-react with" insulin are used synonymously in this description, they must be construed in the broadest sense without being limited to these exemplifications. Whether an antibody "reacts with" an antigen (compound) such as insulin can be determined by solid-phase antigen ELISA, competitive ELISA, and sandwich ELISA described later and can also be identified by a method utilizing the principle of surface plasmon resonance (SPR method). The SPR method can be performed using devices, sensors, and reagents commercially available under the name of BIACORE (registered trademark).

Stating that an antibody of the present invention "does not react with" a compound suggests that the antibody of the present invention does not substantially react with the compound, while stating "not substantially reacting" suggests that enhanced reactivity of the antibody of the present invention is not recognized when BIACORE (registered trademark) T100 is used for immobilizing and assaying the antibody of the present invention based, for example, on the SPR method. In particular, it means that the reactivity between an antibody and a compound is not significantly different from the reactivity in the control experiment (with no compound added). Needless to say, it can be confirmed that an antibody is "not substantially reacting" with a compound by a method well known to those skilled in the art, in addition to the SPR method.

An antibody of the present invention may recognize the entire insulin molecule or a portion as an antigen.

A monoclonal antibody (66221-antibody) produced by a hybridoma (FERM BP-11233) can specifically be cited as the "first monoclonal antibody" and another monoclonal antibody (66226-antibody) produced by a hybridoma (FERM BP-11234) can be cited as the "second monoclonal antibody."

The antibodies of the present invention can be easily produced by dissolving insulin as an antigen (immunogen) in solvent, such as phosphate-buffered saline (PBS), and administering this solution to immunize an animal. The immunization may be performed using an emulsion after adding an appropriate adjuvant to the solution as required. The adjuvant may be a widely used adjuvant, such as water-in-oil emulsion, water-in-oil-in-water emulsion, oil-in-water emulsion, liposome, or aluminum hydroxide gel as well as a protein or peptidic substance derived from biogenic components. For example, Freund's incomplete or complete adjuvant can be used in a preferred manner. Although not particularly limited, it is desired that the administration route, administered dose, and administration time of the adjuvant are appropriately selected such that a desired immune response can be enhanced in an animal to be immunized by the antigen.

Although the choice of the animal used for the immunization is not particularly limited, it is preferably a mammal and can be a mouse, rat, bovine, rabbit, goat, and sheep, although a mouse is more preferred. The animal may be immunized in accordance with a common technique, e.g., the immunization can be achieved by subcutaneously, intracutaneously, intavenously, or intraperitoneally injecting the animal with a solution of an antigen, preferably a mixture with the adjuvant. Since an immune response is generally different depending on the type and strain of an animal to be immunized, it is desirable that an immunization schedule is appropriately set depending on the animal to be used. Preferably, the antigen administration is repeated several times after the initial immunization.

A method of producing a monoclonal antibody itself can be performed in conformity with a method described, for example, in Antibodies, A Laboratory Manual (Cold Spring Harbor Laboratory Press, (1988)). The following operations are subsequently performed to acquire a monoclonal antibody, but these operations are not limitations.

After the final immunization, the hybridoma can be produced by extracting spleen or lymph node cells, which are antibody-producing cells, from an immunized animal and by fusing these cells with proliferative myeloma cells. It is preferred that cells having high antibody-producing ability (quantitative and qualitative) be used for the cell fusion and that the myeloma cells be compatible with the animal from which the antibody-producing cells to be fused are derived. The cell fusion can be performed in accordance with a method known in the art, and a polyethylene glycol method, a method using Sendai virus, or a method utilizing electric current can be employed. The acquired hybridoma can be proliferated in accordance with a known method, and the desired hybridoma can be selected while identifying the property of the produced antibody. The hybridoma can be cloned by a known method such as a limiting dilution or soft agar method.

Selection of the hybridoma producing the first monoclonal antibody will be described.

The hybridoma can efficiently be selected at the selection stage, considering the condition under which the produced antibody is actually used in the assay. For example, the hybridoma can be acquired by selecting a hybridoma that produces an antibody reactive with insulin through ELISA or RIA. In particular, first, the solid-phase antigen ELISA, reacting a monoclonal antibody in the culture supernatant with solid-phased insulin and subsequently reacting labeled anti-IgG antibodies with solid-phased insulin, is used for selecting a hybridoma that produces a monoclonal antibody that is highly reactive with insulin.

A monoclonal antibody having a desired property can be produced by the mass cultivation of the hybridoma selected in this manner. A method of mass cultivation is not particularly limited and can include, e.g., a method of producing the monoclonal antibody in culture media by cultivating the hybridoma in appropriate culture media and a method of producing the antibody in abdominal dropsy by injecting the hybridoma into the abdominal cavity of a mammal for proliferation. The monoclonal antibody can be purified by appropriately combining anion exchange chromatography, affinity chromatography, the ammonium sulfate fractionation method, the PEG fractionation method, and the ethanol fractionation method.

Hybridoma producing the second monoclonal antibody can be selected by appropriately combining the following methods: a selection method using insulin bound to the first monoclonal antibody in place of the solid-phased insulin used in case of selection of the hybridoma producing the first monoclonal antibody (a method in which insulin is bound to the first solid-phased monoclonal antibody to observe the sandwich formation with a candidate of the second monoclonal antibody), a selection method in which the candidate of the second monoclonal antibody is solid-phased to observe the reactivity with an insulin-antibody complex formed by incubating the first monoclonal antibody and insulin in advance, or a method in which antibodies exhibiting no reactivity with insulin are selected using BIACORE (registered trademark) T100 for identification.

The antibodies related to the present invention can be whole antibody molecules as well as functional fragments having antigen-antibody reaction activity. The antibodies can be those acquired through immunization of animals, by a gene recombination technique, or chimeric antibodies. The functional fragments of antibodies include $F(ab')_2$ and Fab', and these functional fragments can be produced by processing the antibodies acquired as described above with a proteolytic enzyme (e.g., pepsin or papain).

One or both of the first and second monoclonal antibodies of the present invention may be immobilized on an insoluble carrier or labeled with a well-known and commonly used labeling material, which we will describe later. We may refer to them as "immobilized (solid phase) antibodies" and labeled antibodies, respectively. Such immobilized or labeled antibodies are included in the scope of the present invention. For example, an immobilized antibody can be produced by causing an insoluble carrier to physically adsorb or chemically bind to a monoclonal antibody (a suitable spacer may exist in between them). The insoluble carrier can be made of a polymer base material such as a polystyrene resin, an inorganic base material such as glass, and a polysaccharide base material such as cellulose and agarose, and the shape is not particularly limited and can be selected arbitrarily. For example, the insoluble carrier may be in the shape of a plate (e.g., microplate and membrane), beads, particles (e.g., latex particles and colloidal gold particles), or a cylinder (e.g., test tube).

The amount of insulin in a sample may be determined using a labeled antibody, such as a labeled protein A or G, which can bind to the second monoclonal antibody of the present invention. Labeling materials for antibodies include enzymes, fluorescent materials, chemiluminescent materials, biotin, avidin, radio isotopes, colloidal gold particles, and colored latex. Labeling materials can be bound to the antibodies by conventional methods, such as glutaraldehyde, maleimide, pyridyl disulfide, or periodic acid method. However, the types of immobilized or labeled antibody and the producing methods are not limited to those described above. For example, when an enzyme such as peroxidase or alkaline phosphatase is used as a labeling material, the enzymatic activity may be assayed using a specific substrate of the enzyme, e.g., o-phenylenediamine (OPD) or 3,3',5,5'-tetramethylbenzidine for horseradish peroxidase (HRP), and p-nitrophenyl phosphate for ALP. When biotin is used as the labeling material, at least avidin or enzyme-modified avidin is normally used in the reaction.

In this description, an "insoluble carrier" may be represented as a "solid phase," and physically or chemically supporting an antigen or antibody with an insoluble carrier or the supporting state may be represented as "immobilizing," "immobilized," "solid phase," "sensitization," or "adsorption." The term "detection" or "measurement" must be construed in the broadest sense, including the existence proof and/or quantitation of insulin.

"Samples," which contain the analyte to be detected in an assay using the antibodies of the present invention, can mainly be body fluids derived from a living body (organism). The body fluids can specifically include, but are not limited to, blood (whole blood), serum, plasma, urine, saliva, phlegm, pancreas extract, lacrimal fluid, otorrhea, and prostatic fluid.

The form of an assay reagent (kit) provided by the present invention is not particularly limited as long as the reagent is capable of assaying insulin. Representative label immunoassays, i.e., ELISA and immunochromatography, and a representative particle agglutination immunoassay, i.e., latex immunoagglutination assay (LITA), will hereafter be considered examples and described.

Label-Linked Immunoassay: ELISA

The form of the assay reagent (kit) for detecting insulin present in a sample can include the following elements:
(a) a solid phase (such as a plate) with the first monoclonal antibody immobilized, and
(b) the second monoclonal antibody labeled with a labeling material.

The solid phase (such as a plate) with the first monoclonal antibody immobilized captures insulin in a sample to form an insulin-antibody complex. The second monoclonal antibody labeled with the labeling material reacts with the insulin-antibody complex to form a sandwich, and the insulin in the sample can be assayed by measuring an amount of the labeling material by a method suitable for the labeling material. With regard to specific methods for configuring the assay reagent (kit), such as a method for immobilizing the first monoclonal antibody to the solid phase and a method for labeling the second monoclonal antibody with the labeling material, well-known techniques can be used without limitation, in addition to those described here. Although this configuration can be formed as a homogeneous assay system, it is preferred that the configuration is formed as a heterogeneous assay system.

Aspect [19] can be recommended as a particularly preferred form (the insulin assay reagent of any one of aspects [13], [15], [16] and [17], wherein the first monoclonal antibody is immobilized to a solid phase, the second monoclonal antibody is labeled with a labeling material, and insulin is assayed by ELISA).

Considering the sensitivity and specificity of the assay reagent, the configuration reversed from the above can be employed as follows:

(a) the first monoclonal antibody labeled with a labeling material, and (b) a solid phase (such as a plate) with the second monoclonal antibody immobilized.

In case of this configuration, the test sample is preferably mixed with a solution containing the first monoclonal antibody labeled with a labeling material to form the insulin-antibody complex in the solution in advance, and the insulin-antibody complex is added to the solid phase with the second monoclonal antibody immobilized. In this configuration, with the aim of enhancing the sensitivity, two or more monoclonal antibodies having different recognition sites can be used in a preferred manner as the first monoclonal antibody labeled with a labeling material, i.e., aspect [15] (the insulin assay reagent of aspect [13], wherein the first monoclonal antibody consists of two or more monoclonal antibodies having different recognition sites).

Aspect [20] can be recommended as a particularly preferred form (the insulin assay reagent of any one of aspects [13], [15], [16], and [17], wherein the first monoclonal antibody is labeled with a labeling material, the second monoclonal antibody is immobilized to a solid phase, and insulin is assayed by ELISA).

Label-Linked Immunoassay: Immunochromatography

Typical immunochromatography is configured such that in order of distance from the edge in the longitudinal direction on a sheet-shaped solid-phase support such as a membrane, a test sample solution continuously moves because of capillarity (capillary phenomenon) through: "1. a sample loading site," "2. a labeled reagent site that holds, in a spreadable manner on the membrane, a labeled reagent containing the first monoclonal antibody (the first monoclonal antibody is labeled with a labeling material such as colloidal gold particles)," and "3. a capture reagent site with the second monoclonal antibody immobilized for capturing the complex of the first monoclonal antibody labeled with the labeling material and insulin."

In particular, when a predetermined amount of a test sample containing insulin is added to the sample loading site, the sample infiltrates the labeled reagent site in the course of spreading and moving on the solid-phase support, and the insulin binds to the labeled reagent (containing the first monoclonal antibody) to form a labeled reagent-insulin complex (an insulin-labeled reagent complex). The labeled reagent-insulin complex continues spreading and moving on the membrane, and when infiltrating into the capture reagent site on the membrane, which contains the second monoclonal antibody, the complex is captured by the capture reagent immobilized on the solid-phase support to form a capture reagent (second monoclonal antibody)-insulin-labeled reagent (first monoclonal antibody) complex at the site. The presence of the analyte can be determined by detecting the labeled reagent by a method of your choice, e.g., detecting the appearance of agglutination (agglutination image/picture) in the case of visible colloidal gold particles and detecting the chromogenic reaction due to addition of a substrate in case of enzyme.

Although there are separate descriptions for "1. the sample loading site" and "2. a labeled reagent site that holds, in a spreadable manner on the membrane, a labeled reagent containing the first monoclonal antibody (the first monoclonal antibody is labeled with a labeling material such as colloidal gold particles)" in order of the movement direction of the test sample to facilitate understanding, those skilled in the art can obviously understand that well-known forms/configurations may be employed, such as a stacked structure in the order of "1" and "2" from the top.

In immunochromatography, an insulin-antibody complex is formed at the time of passage of the test sample through "2. a labeled reagent site that holds, in a spreadable manner on the membrane, a labeled reagent containing the first monoclonal antibody (the first monoclonal antibody is labeled with a labeling material such as colloidal gold particles)," and therefore, with a view to enhance the sensitivity, as in the case of ELISA, two or more monoclonal antibodies having different recognition sites can be used in a preferred manner as the first monoclonal antibody labeled with the labeling material, i.e., aspect [15] (the insulin assay reagent of aspect [13], wherein the first monoclonal antibody consists of two or more monoclonal antibodies having different recognition sites).

Aspect [20] can be recommended a particularly preferred form (the insulin assay reagent of any one of aspects [13], [15], [16], and [17], wherein the first monoclonal antibody is labeled with a labeling material, the second monoclonal antibody is immobilized to a solid phase, and insulin is assayed by immunochromatography).

Turbidimetric Immunoassay: LTIA

Four embodiments, A to D, of an assay reagent (kit) for detecting insulin present in a sample may comprise the following:

A. (a) latex particles with the first monoclonal antibody immobilized and (b) latex particles with the second monoclonal antibody immobilized;

B. (a) latex particles with the first monoclonal antibody immobilized and (b) the second monoclonal antibody;

C. (a) the first monoclonal antibody and (b) latex particles with the second monoclonal antibody immobilized; and D. (a) latex particles with both the first and second monoclonal antibodies immobilized.

These assay reagents (kits) can be used in LTIA in a preferred manner. The latex particles used in A to D can be selected appropriately in terms of particle diameter and type in order to acquire the desired capability, such as enhanced sensitivity. The latex particles may be those suitable for carrying an antigen or antibody. For example, the latex particles may be of polystyrene, styrene-sulfonic acid (sulfonate) copolymer, styrene-methacrylic acid copolymer, acrylonitrile-butadiene-styrene copolymer, vinyl chloride-acrylic ester copolymer, or vinyl acetate-acrylic acid ester copolymer. Although the shape of the latex particles is not particularly limited, it is preferable that an average particle diameter is defined such that the produced aggregate, as a result of the agglutination reaction between the antibody (or antigen) on the latex particle surface and the analyte, has a size sufficient to be visibly or optically detected. The average particle diameter is preferably 0.02 to 1.6 µm and particularly 0.03 to 0.5 µm. Particles made of metallic colloid, gelatin, liposome, microcapsule, silica, alumina, carbon black, metallic compound, metal, ceramics, or magnetic material can be used instead of the latex particles.

For example, the reagent of LTIA used in clinical examinations is usually provided in the form of the first and second reagent solutions, which are sequentially mixed with the test sample in use. One or both (a) and (b) in each of the forms A to D can be included in the first or second reagent solution. The methods of including (a) and (b) may be appropriately selected depending on the particulars of the measuring device for the clinical examination and the design of the assay reagent (such as capability and usability). Although, preferably, both (a) and (b) of the form A are included in the second reagent, (a) and (b) of the form A can also be included in the first and second reagents, respectively, in a preferred manner.

Aspect [18] can be recommended as a particularly preferred form (the insulin assay reagent of any one of aspects [13] [15], [16], and [17], wherein the first and second monoclonal antibodies are immobilized to the latex and insulin is assayed by latex immunoagglutination assay).

Although the embodiments of the present invention have been described by considering aspect [3], which is a representative form of the present invention, as an example, those skilled in the art can obviously understand that the present invention can be implemented in various forms, e.g., using a polyclonal antibody for the first antibody, as in aspect [4], and two or more monoclonal antibodies having different recognition sites for the first antibody, as in aspect [5], on the condition that an antibody for the "insulin-antibody complex" is used.

Although the present invention will be described in more detail with reference to examples, the present invention is not limited to these examples.

EXAMPLES

First Test Example

Method of Producing Monoclonal Antibody of the Present Invention

1. Preparation of Immunizing Antigen

After human insulin (Fitzgerald Industries International, 30-A151) was mixed 1:1 with complete Freund's adjuvant (Wako Pure Chemical Industries, Ltd.), connected syringes were used for producing emulsion to be used as the immunizing antigen.

2. Production of Hybridoma

The immunizing antigen was subcutaneously injected into the dorsal regions of female BALB/c mice (20 to 50 μg per mouse). Immunization as repeated twice per week. After three weeks from the start of immunization, spleen was extracted from a mouse having a high antibody titer in the blood sample, and cell fusion was performed by a routine procedure using 50% PEG 1450 (Sigma). SP2/O myeloma cells were used. The acquired fused cells were suspended at $2.5 \times 10^6$/mL (as spleen cells) in RPMI 1640 media that contained HAT, 15% fetal bovine serum, and 10% BM-Condimed HI Hybridoma Cloning Supplement (Roche Diagnostics K.K.) were dispensed in a 96-well culture plate in 0.2-mL aliquots. The fused cells were cultivated at 37° C. in a 5% $CO_2$ incubator.

3. Screening of Hybridoma Producing the First Monoclonal Antibody

After seven days from the cell fusion, the culture supernatant was used for performing solid-phase antigen ELISA described later as primary screening to select wells that exhibit a high reactivity to insulin as primary positive wells. The cells in the primary positive wells were serially passaged in a 24-well plate. After two days of serial cultivation, the culture supernatant was used to perform competitive ELISA described later as a secondary screening to select wells that exhibited a high reactivity to insulin as secondary positive wells.

3-1. Production of the Solid-Phase Antigen ELISA Plate

Insulin prepared at a concentration of 1 μg/mL with 10 mM PBS (pH 7.2) containing 150 mM sodium chloride was solid-phased as a screening antigen on a 96-well plate at 50 μL/well and was allowed to stand overnight at 4° C. After washing three times with 400 μL/well of PBS solution containing 0.05% TWEEN (registered trademark) 20 and 0.1% ProClin 300 (Supelco; PBST), PBST containing 1% BSA (BSA-PBST) was dispensed at 100 μL/well and allowed to stand one hour at room temperature for blocking to produce an ELISA plate. The ELISA plate was washed three times with PBST and used for ELISA tests described in the examples by adding reagents.

3-2. Solid-Phase Antigen ELISA (i) Mouse antiserum or culture supernatant of the fused cells diluted stepwise with BSA-PBST was dispensed on a solid-phase antigen ELISA plate at 50 μL/well and allowed to stand one hour at room temperature.

(ii) After washing three times with PBST, a solution HRP-Gt F(ab')$_2$-Anti-Mouse Ig's (BioSource, AM14404) diluted 5000 times with BSA-PBST dispensed a 50 μL/well and allowed to stand one hour at room temperature.

(iii) After washing three times with PBST, OPD (Tokyo Chemical Industry Co., Ltd.) was dissolved at 2 mg/mL in 0.2 M citrate buffer solution containing 0.02% hydrogen peroxide/water (hereinafter, substrate-dissolving solution), added at 50 μL/well, and allowed to stand one hour at room temperature.

(iv) Furthermore, 1.5 N sulfuric acid containing 1 mM EDTA (hereinafter, reaction stop liquid) was added at 50 μL/well, and absorbance was measured at a wavelength of 492 nm using TITERTEK (registered trademark) Multiskan Plus MK II (Flow Laboratories Inc).

3-3. Competitive ELISA (i) Solutions of human insulin (Fitzgerald Industries International, 30-A151) diluted with BSA-PBST at 0, 2.5, 5, and 10 μg/mL were dispensed on a solid-phase antigen ELISA plate at 25 μL/well.

(ii) Culture supernatant of the fused cells diluted to 5 and 25 times with BSA-PBST or undiluted solution thereof was then dispensed at 25 μL/well and allowed to stand one hour at room temperature.

(iii) The subsequent operations were performed in the same manner as steps (ii) to (iv) of "3-2. Solid-Phase Antigen ELISA" described above.

4. Screening of Hybridoma Producing the Second Monoclonal Antibody

After seven days from the cell fusion, the culture supernatant was used for performing sandwich ELISA described later to select wells exhibiting a high reactivity to insulin bound to the first F(ab')$_2$ monoclonal antibody collected in advance by cloning and monoclonal antibody collection described later.

4-1. Sandwich ELISA (i) The first monoclonal antibody (in this case, 66221-antibody) was treated to prepare F(ab')$_2$ using the IMMUNOPURE (registered trademark) F(ab')$_2$ Preparation Kit (Pierce, prod#44888).

(ii) The first F(ab')$_2$ monoclonal antibody prepared at a concentration of 2 μg/mL with PBS solution was solid-phased on a 96-well plate at 50 μL/well and was allowed to stand overnight at 4° C. After washing three times with 400 μL/well of PBST, BSA-PBST was dispensed at 100 μL/well and allowed to stand one hour at room temperature for blocking in order to produce an ELISA plate.

(iii) Solution of human insulin (Fitzgerald Industries International, 30-A151) diluted with BSA-PBST at 0.5 μg/mL was dispensed on the ELISA plate at 50 μL/well and allowed to stand one hour at room temperature.

(iv) After washing three times with PBST, the culture supernatant of the fused cells diluted stepwise with BSA-PBST was dispensed at 50 µL/well and allowed to stand one hour at room temperature.

(v) After washing three times with PBST, a solution of HRP-Gt-Anti-Mouse IgG-Fc (Bethyl Laboratories, A90-131P) diluted 10000 times with BSA-PBST was dispensed at 50 µL/well and allowed to stand one hour at room temperature.

(vi) After washing three times with PBST, OPD (Tokyo Chemical Industry) was dissolved at 2 mg/mL in the substrate-dissolving solution, added at 50 µL/well, and allowed to stand one hour at room temperature.

(vii) The reaction stop liquid was added at 50 µL/well, and absorbance was measured at 492 nm using TITERTEK (registered trademark) Multiskan Plus MK II (Flow Laboratories).

5. Cloning and Monoclonal Antibody Collection

Hybridomas selected by the screenings of 3. and 4. described above were cloned by a limiting dilution method to acquire hybridomas 66221 and 66226, respectively. To collect the monoclonal antibodies produced by the hybridomas, the hybridomas were intraperitoneally administered, in an amount corresponding to $0.5 \times 10^6$ cells, to a 12-week-old female BALB/c mouse intraperitoneally injected with 0.5 mL of pristane two weeks earlier. The ascites were collected after 14 days, and the supernatants were acquired by centrifugation. The supernatants were mixed with the same amount of adsorption buffer solution (3 mol/L NaCl, 1.5 mol/L Glycine-NaOH buffer solution, pH 8.5) and then filtrated. The filtrates were passed through a protein A sepharose column equilibrated with adsorption buffer solution to adsorb the antibodies in the filtrates using the column, and the antibodies were eluted with 0.1 mol/L citrate buffer solution (pH 3.0). After neutralizing the eluate with 1 mol/L Tris-HCl buffer solution (pH 8.0), dialysis was performed with PBS to collect the antibodies.

The antibodies, referred to as the 66221-antibody and 66226-antibody, were subsequently used in tests.

Hybridomas producing the 66221-antibody and 66226-antibody were deposited at International Patent Organism Depositary, National Institute of Advanced Industrial Science and Technology (Address: Tsukuba Central 6, 1-1-1 Higashi, Tsukuba, Ibaraki, Japan) on Apr. 8, 2009 under the accession numbers FERM P-21800 and FERM P-21801, respectively. Subsequently, they were transferred to the Budapest Treaty on Feb. 17, 2010, based on the original deposition, under the accession numbers FERM BP-11233 and FERM BP-11234, respectively.

Second Test Example

Cross-Reactivity of Monoclonal Antibody of the Present Invention with Proinsulin and Insulin Analogs A test was performed using BIACORE (registered trademark) T100 for cross-reactivity of the 66221-antibody and the 66226-antibody with proinsulin and insulin analogs. For the insulin analogs, insulin analog formulations such as insulin lispro, insulin aspart, insulin glargine, and insulin detemir were used.

1. Reagents and Instruments
1-1. Monoclonal Antibodies
(i) 66221-antibody: 2.30 mg/mL
(ii) 66226-antibody: 3.99 mg/mL 1-2. Analytes
(i) recombinant human insulin: Fitzgerald Industries International, 30-A151
(ii) proinsulin: IRR Proinsulin, Human, for Immunoassay; NIBSC code: 84/611
(iii) insulin analog formulations
(1) insulin lispro, 100 units/mL: Eli Lilly Japan K.K.
(2) insulin aspart, 100 units/mL: Novo Nordisk Pharma Ltd.
(3) insulin glargine, 100 units/mL: sanofi-aventis K.K.
(4) insulin detemir, 100 units/mL: Novo Nordisk Pharma Ltd.

1-3. BIACORE (registered trademark) devices and a dedicated reagent set (BIACORE: currently, GE Healthcare; although (i) to (viii) described below are products and catalog numbers of then BIACORE, these are currently available from GE Healthcare.)
(i) BIACORE (registered trademark) T100: BIACORE, JJ-1037-02
(ii) Series S Sensor Chip CM5: BIACORE, BR-1005-30
(iii) Amine Coupling Kit: BIACORE, BR-1000-50
(iv) Acetate 5.0: BIACORE, BR-1003-51
(v) α-Mouse Immunoglobulins: BIACORE, BR-1005-14
(vi) Glycine 1.5: BIACORE, BR-1003-54
(vii) Glycine 2.0: BIACORE, BR-1003-55
(viii) HBS-EP+ 10× (Running Buffer): BIACORE, BR-1006-69 (prepared at pH 8.5 with NaOH and diluted 10 times with purified water on use)

2. Test Method

The 66221-antibody or 66226-antibody was captured by α-mouse immunoglobulins immobilized on a sensor chip, and insulin, proinsulin, and various insulin analog formulations were added as analytes to evaluate the reactivity therewith. The specific operational procedure used is as follows.

(i) α-Mouse immunoglobulins were immobilized on Sensor Chip CM5 (in accordance with the accompanying instruction manual).

(ii) The 66221-antibody or 66226-antibody was diluted with HBS-EP+ (pH 8.5) to 5 µg/mL and added at a flow rate of 30 µL/min for 300 seconds.

(iii) Various antigens were diluted with HBS-EP+ (pH 8.5) to 10 ng/mL and added at two concentrations of 0 and 10 ng/mL for 120 seconds each. A time for free-running dissociation was set to 120 seconds in this case.

(iv) Glycine 1.5 and Glycine 2.0 were mixed 1:1 to form regenerating solution, and regenerating treatment was performed for 180 seconds.

3. Results 3-1. Results of Reaction with Insulin

Figure 2:
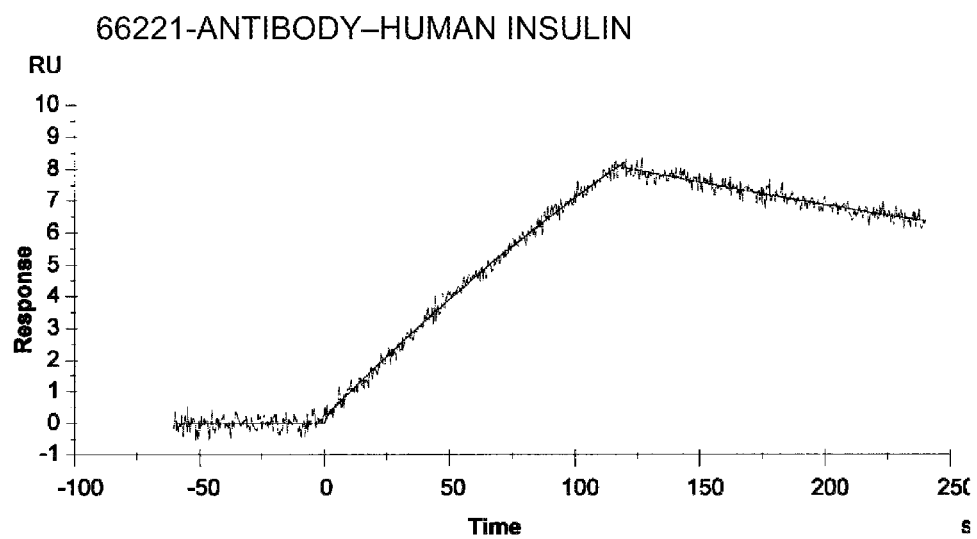
FIG. 2 is a diagram of the results of a test using BIACORE (registered trademark) T100 for examining reactivity of a 66221-antibody with insulin.
Figure 3:
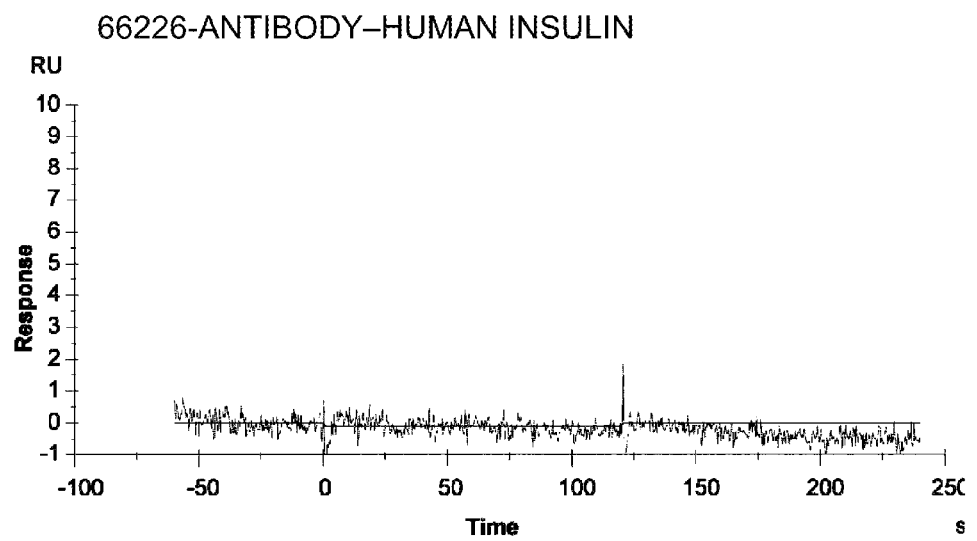
FIG. 3 is a diagram of the results of a test using BIACORE (registered trademark) T100 for examining reactivity of a 66226-antibody with insulin.
Figure 4:
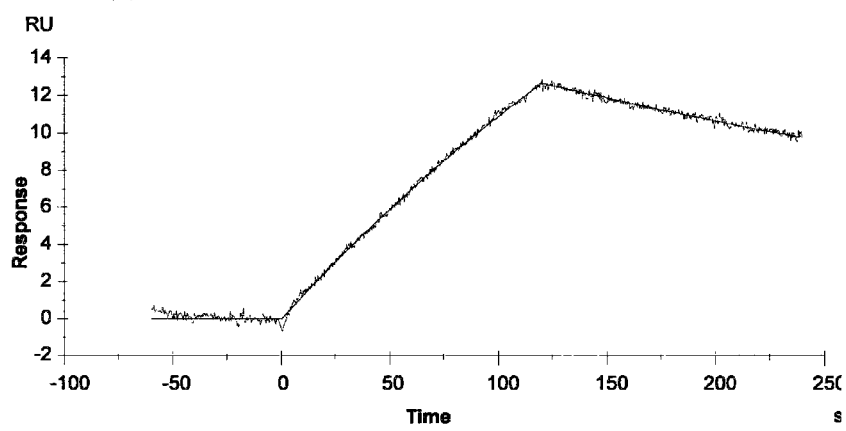
Figure 2:
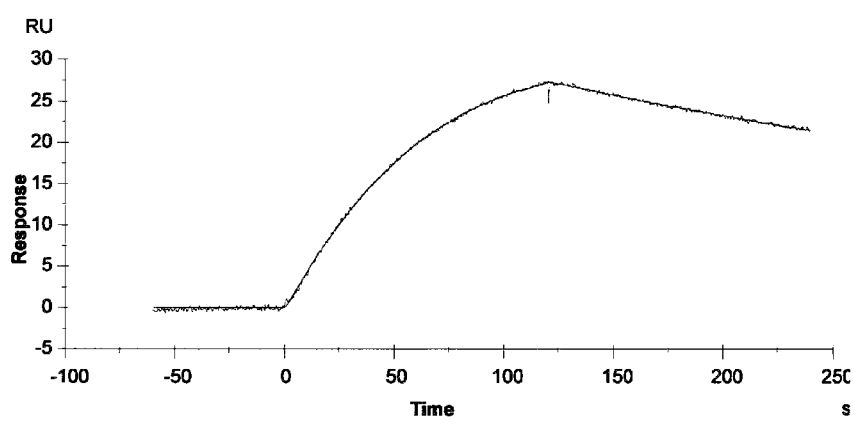
Figure 5:
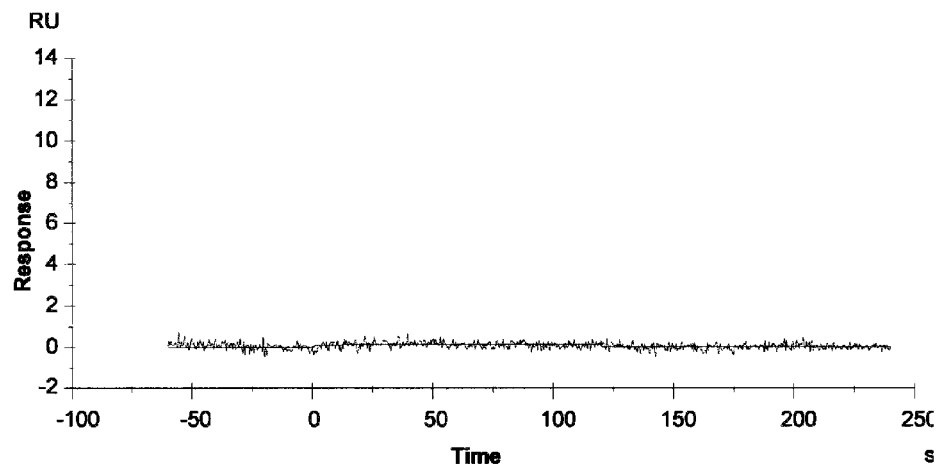
Figure 2:
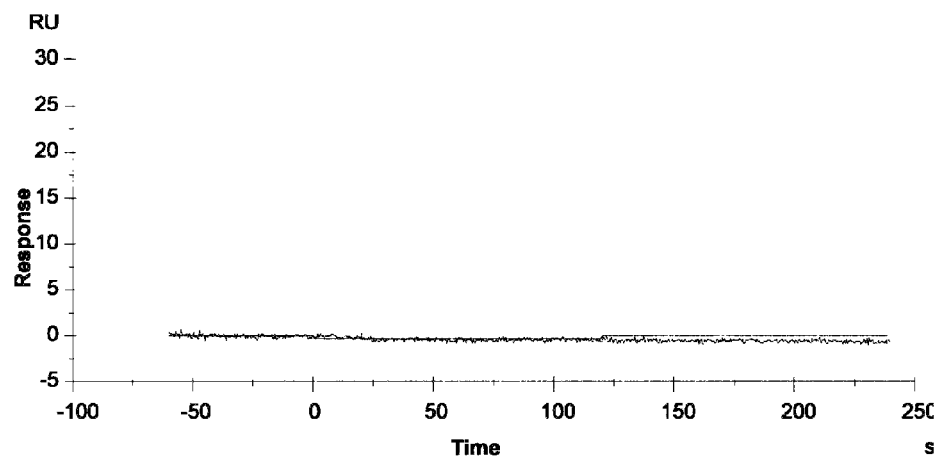

For the 66221-antibody and 66226-antibody, the reactivity with insulin was checked using BIACORE (registered trademark) T100. The results are depicted in FIGS. 2 and 3. The 66221-antibody showed a reactivity of 8.5 RU at an insulin concentration of 10 ng/mL (FIG. 2). In contrast, no reactivity was detected for the 66226-antibody (FIG. 3). The vertical axis (RU) indicates a unit unique to the BIACORE (registered trademark) assay system and represents a mass change due to reaction on the sensor surface.

3-2. Results of Reaction with Proinsulin and Insulin Analog Formulations

For the 66221-antibody and 66226-antibody, the reactivity with proinsulin or various insulin analog formulations (insulin lispro, insulin aspart, insulin glargine, and insulin detemir) was checked using BIACORE (registered trademark) T100. The result is depicted in FIGS. 4-1, 4-2, 5-1, and 5-2. In each case, at an antigen concentration of 10 ng/mL, responses of 5.5 to 13 RU were detected for the 66221-antibody. In contrast, no reactivity was detected for the 66226-antibody.

Example 1

Assay of Insulin Using Combination of Monoclonal Antibodies of the Present Invention 1

1. Production of Latex Particles

A glass reaction container (capacity: 2 L) equipped with a stirring machine, reflux condenser, thermal sensing device, nitrogen introduction tube, and jacket was filled with 1100 g of distilled water, 200 g of styrene, 0.2 g of sodium styrene sulfonate, and aqueous solution of 1.5 g of potassium peroxodisulfate dissolved in 50 g of distilled water, and after the inside of the container was replaced with nitrogen gas, polymerization was performed for 48 hours while stirring at 70° C.

After the end of polymerization, the solution was filtrated with a filter paper to extract latex particles. A transmission electron microscope apparatus (JEOL Ltd., model "JEM-1010") was used for imaging the latex particles at a magnification of 10000 times and analyzing diameters of at least 100 acquired latex particles to determine the average particle diameter. The obtained average particle diameter was 0.3 µm.

2. Preparation of the Anti-Insulin Antibody-Sensitized Latex Particle 2-1. Production of 66221-Antibody-Sensitized Latex Particle Solution To 1.0% latex solution having an average particle diameter of 0.3 µm [in 5 mM Tris buffer solution (hereinafter, Tris-HCl), pH 8.5], 66221-antibody solution, diluted to 0.60 mg/mL with the same volume of 5 mM Tris-HCl (pH 8.5), was added and stirred at 4° C. for two hours. The same volume of 5 mM Tris-HCl (pH 8.5) containing 0.5% BSA was subsequently added and stirred at 4° C. for one hour. After the solution was centrifuged and supernatant removed, the precipitate was resuspended in 5 mM Tris-HCl (pH 8.5) to produce a 66221-antibody-sensitized latex particle solution.

2-2. Production of 66226-Antibody-Sensitized Latex Particle Solution

The latex having an average particle diameter of 0.3 µm was used for producing a 66226-antibody-sensitized latex particle solution in the same manner as above.

3. Preparation of Reagents 3-1. Preparation of the First Reagent

Five (5) millimolar Tris-HCl (pH 8.5) containing 500 mM of sodium chloride and 0.2% BSA was used as the first reagent.

3-2. Preparation of the Second Reagent

The same volumes of the 66221-antibody—and 66226-antibody-sensitized latex particle solutions were mixed and diluted with 5 mM Tris-HCl (pH 8.5) such that absorbance of 5.0 Abs was achieved at a wavelength of 600 nm to prepare the second reagent.

4. Assay

The first and second reagents were combined, and insulin concentration-dependent formation of particle aggregate was identified using a Hitachi 7170 Automated Analyzer. In paticular, 150 µL of the first reagent was added to 10 µL of insulin solutions at concentrations of 0, 5, 25, 50, 100, and 200 µU/mL and heated at 37° C. for 5 minutes. Subsequently, 50 µL of the second reagent was added, followed by stirring. After five minutes, changes in absorbance associated with agglutination formation were measured at 570 nm and sub-wavelength of 800 nm.

TABLE 1

| Insulin concentration µU/mL | Absorbance mAbs |
|---|---|
| 0 | 11.4 |
| 5 | 23.6 |
| 25 | 40.9 |
| 50 | 57.7 |
| 100 | 82.9 |
| 200 | 117.1 |

5. Assay Result

Table 1 shows that sensitivity increases depending on the insulin concentration and can be quantitated.

Example 2

Assay of Insulin Using Combination of Monoclonal Antibodies of the Present Invention 2

Either the 66221-antibody or 66226-antibody was solid-phased, and the rest was used as a secondary antibody to test the reactivity with proinsulin and insulin analogs by ELISA.

1. Antibodies and Antigens Used (1) Monoclonal Antibodies 66221-antibody: 2.30 mg/mL 66226-antibody: 3.99 mg/mL (2) Antigens Insulin, proinsulin, and insulin analog formulations (insulin lispro, insulin aspart, insulin glargine, and insulin detemir) used were the same as the second test example.

2. ELISA Method (i) The solution of the 66221-antibody or 66226-antibody diluted to 2 µg/mL with PBS was solid-phased in a 96-well plate at 50 µU/well and allowed to stand two hours at room temperature.

(ii) After washing three times with 400 µU/well of PBST, BSA-PBST was dispensed at 100 µL/well and allowed to stand one hour at room temperature for blocking in order to produce an ELISA plate.

(iii) The solution of each of human insulin, proinsulin, and insulin analog formulations diluted with BSA-PBST to 0, 1, 5, and 10 ng/mL was dispensed on the ELISA plate at 50 µL/well and allowed to stand one hour at room temperature.

(iv) After washing three times with PBST, a solution of a biotin-labeled 66226-antibody or 66221-antibody diluted to 1 µg/mL with BSA-PBST was dispensed at 50 µL/well and allowed to stand one hour at room temperature.

(v) After washing three times with PBST, a solution of IMMUNOPURE (registered trademark) Streptavidin, HRP-Conjugated (PIERCE, Prod#21126) diluted 5000 times with BSA-PBST was dispensed at 50 µL/well and allowed to stand one hour at room temperature.

(vi) After washing three times with PBST, OPD (Tokyo Chemical Industry) was dissolved at 2 mg/mL in the substrate-dissolving solution, added at 50 µL/well, and allowed to stand one hour at room temperature.

(vii) The reaction stop solution was added at 50 µL/well, and absorbance was measured at 492 nm using TITERTEK (registered trademark) Multiskan Plus MK II (Flow Laboratories).

Figure 6:
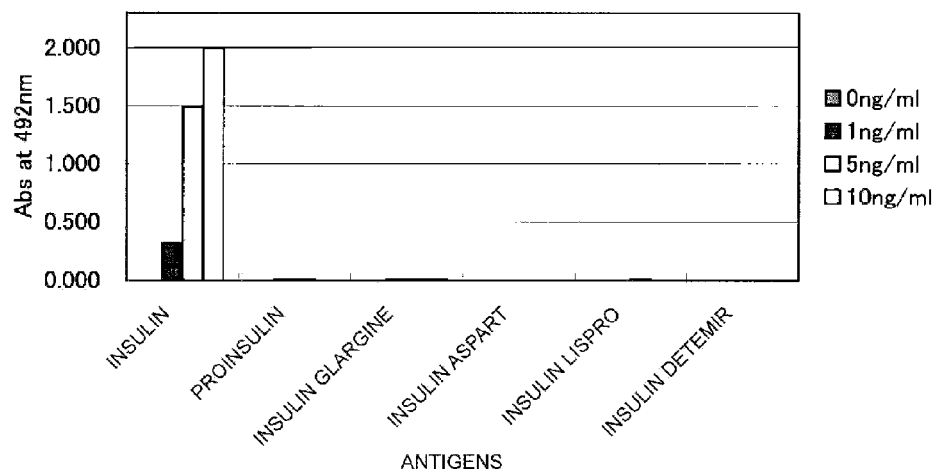
FIG. 6 is a diagram representing the results of an ELISA test for examining reactivity with insulin, proinsulin, and various insulin analog formulations by using the 66221-antibody and 66226-antibody as the primary and secondary antibodies, respectively, with the primary antibody solid-phased on a plate.

3. Result
3-1. 66221 Solid-Phase Antibody Plate Assay Results
Test results are depicted in Table 2 and FIG. 6.
When the 66221-antibody was used as the primary antibody and the 66226-antibody was used as the secondary antibody, a concentration-dependent increase in absorbance was observed for insulin, while no concentration-dependent increase in absorbance was observed for proinsulin and the insulin analog formulations (insulin lispro, insulin aspart, insulin glargine, and insulin detemir).

TABLE 2

| Primary antibody | 66221-antibody | | | | | |
|---|---|---|---|---|---|---|
| Secondary antibody | Biotin-labeled 66226-antibody | | | | | |
| | Antigens | | | | | |
| Antigen concentration | Human insulin | Human proinsulin | Insulin analog formulation/ Insulin glargine | Insulin analog formulation/ Insulin aspart | Insulin analog formulation/ Insulin lispro | Insulin analog formulation/ Insulin detemir |
| 0 ng/ml | 0.000 | 0.000 | 0.000 | 0.000 | 0.000 | 0.000 |
| 1 ng/ml | 0.316 | 0.005 | 0.004 | −0.011 | −0.005 | −0.017 |
| 5 ng/ml | 1.491 | 0.006 | 0.013 | 0.001 | 0.007 | −0.013 |
| 10 ng/ml | 1.995 | −0.013 | 0.008 | −0.006 | 0.000 | −0.016 |

Figure 7:
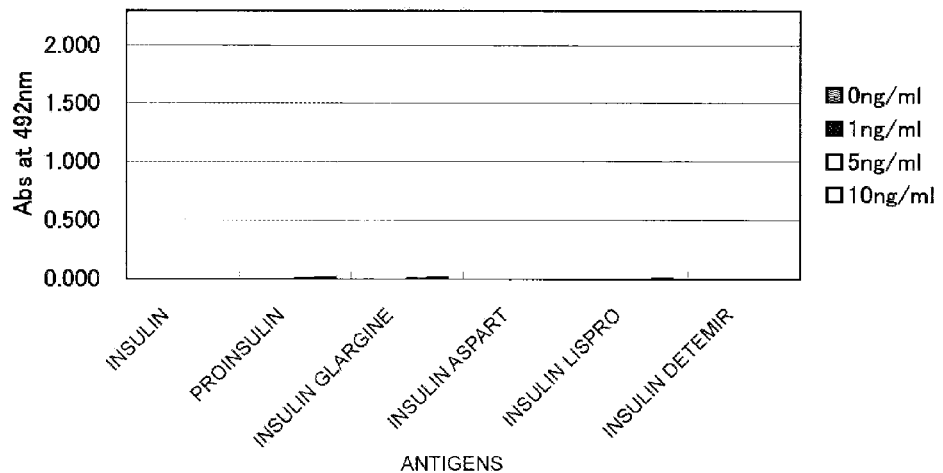
FIG. 7 is a diagram of a result of an ELISA test for examining reactivity with insulin, proinsulin, and various insulin analog formulations using the 66226-antibody and 66221-antibody as the primary and secondary antibodies, respectively, with the primary antibody solid-phased on a plate.

3-2. 66226 Solid-Phase Antibody Plate Assay Results
Test results are depicted in Table 3 and FIG. 7.
When the 66226-antibody was used as the primary antibody and the 66221-antibody was used as the secondary antibody, no concentration-dependent increase in absorbance was observed in any of insulin, proinsulin, and insulin analog formulations (insulin lispro, insulin aspart, insulin glargine, and insulin detemir).

TABLE 3

| Primary antibody | 66226-antibody | | | | | |
|---|---|---|---|---|---|---|
| Secondary antibody | Biotin-labeled 66221-antibody | | | | | |
| | Antigens | | | | | |
| Antigen concentration | Human insulin | Human proinsulin | Insulin analog formulation/ Insulin glargine | Insulin analog formulation/ Insulin aspart | Insulin analog formulation/ Insulin lispro | Insulin analog formulation/ Insulin detemir |
| 0 ng/ml | 0.000 | 0.000 | 0.000 | 0.000 | 0.000 | 0.000 |
| 1 ng/ml | −0.011 | −0.002 | 0.001 | −0.004 | −0.006 | −0.017 |
| 5 ng/ml | −0.010 | 0.004 | 0.004 | −0.003 | −0.002 | −0.011 |
| 10 ng/ml | −0.010 | 0.014 | 0.015 | −0.001 | 0.006 | −0.007 |

4. Discussion
From the above results, it is concluded that insulin can be quantitated without the influence of proinsulin and insulin analog formulations because no cross-reactivity was observed when the 66221-antibody and 66226-antibody were used as the primary and secondary antibodies, respectively. Insulin could not be assayed when the 66226-antibody and 66221-antibody were used as the primary and secondary antibodies, respectively, and it is therefore noted that the 66226-antibody exhibits no reactivity with insulin but reacts with insulin bound to the 66221-antibody. Note that in the cross-reactivity test result of the monoclonal antibodies of the present invention using BIACORE (registered trademark) T100 (the second test example), the 66221-antibody reacted with insulin, proinsulin, and all insulin analog formulations, while the 66226-antibody reacted with none of them.

Therefore, as the reaction mechanism of this assay system, it is speculated that sonic structural change occurs in insulin when the 66221-antibody first binds to insulin and that the 66226-antibody specifically recognizes the structurally changed site to form a sandwich.

Third Test Example

Cross-Reactivity of Monoclonal Antibodies of the Present Invention with Insulin Analogs The test was performed using BIACORE (registered trademark) T100 for cross-reactivity of the 66221-antibody and 66226-antibody with insulin analogs. An insulin analog formulation, i.e., insulin glulisine, was used as the insulin analog.

Figure 8:
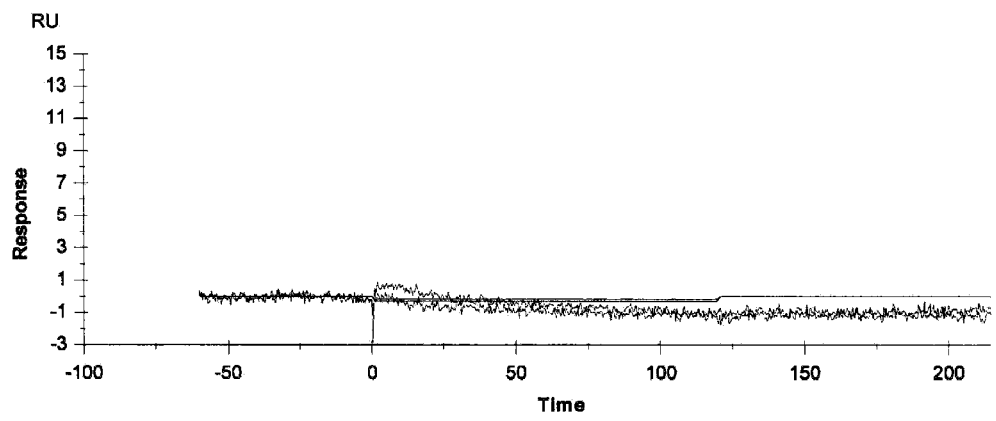
FIG. 8 is a diagram of a result of a test using BIACORE (registered trademark) T100 for examining reactivity of the 66221-antibody (a) and 66226-antibody (b) with an insulin analog formulation, insulin glulisine.
Figure 8:
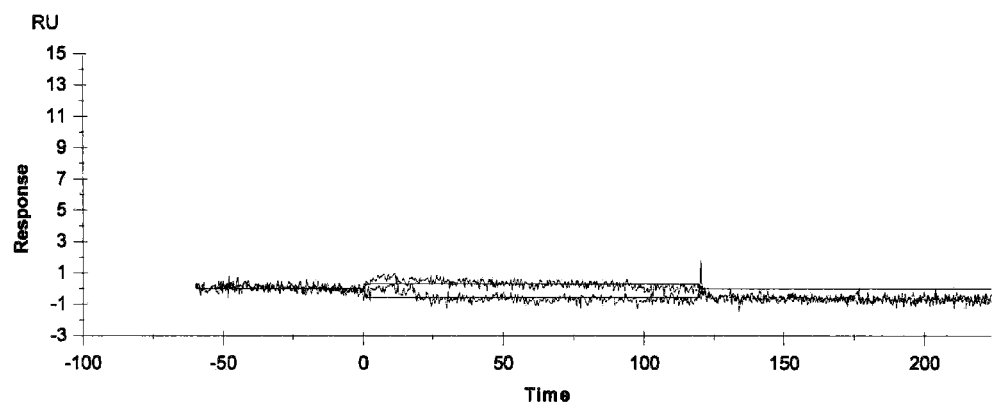

1. Reagents and Instruments
1-1. Monoclonal Antibodies
(i) 66221-antibody: 2.30 mg/mL
(ii) 66226-antibody: 3.99 mg/mL
1-2. Analytes
Insulin Analog Formulation
(i) insulin glulisine, 100 units/mL: sanofi-aventis K.K.
1-3. BIACORE (Registered Trademark) Devices and Dedicated Reagent Set
The BIACORE (Registered Trademark) devices and Dedicated Reagent Set used were the same as the second test example.
2. Test Method
The test was performed in the same manner as the second test example, except that insulin glulisine, an insulin analog formulation, was used as an analyte.
3. Result
3-1. Result of Reaction with Insulin Analog Formulation
For both the 66221-antibody and 66226-antibody, the reactivity with the insulin analog formulation insulin glulisine was checked using BIACORE (registered trademark) T100. The result is depicted in FIG. 8. Neither the 66221- antibody nor 66226-antibody showed reactivity. The vertical axis (RU) indicates a unit unique to the BIACORE (registered trademark) assay system and represents a mass change due to reaction on the sensor surface.

Example 3

Assay of Insulin Using a Combination of Monoclonal Antibodies of the Present Invention 3

Either the 66221-antibody or 66226-antibody was solid-phased, while the other antibody was combined as a secondary antibody to test the reactivity with insulin, proinsulin, and an insulin analog by ELISA.

1. Antibodies and Antigen Types Used
(1) Monoclonal Antibodies
66221-antibody: 2.30 mg/mL
66226-antibody: 3.99 mg/mL
(2) Antigens: insulin, proinsulin, and an insulin analog formulation (insulin glulisine)

2. ELISA Method

The same method as in Example 2 is performed, except that insulin glulisine was used as the insulin analog formulation.

3. Result 3-1. 66221 Solid-Phase Antibody Plate Assay Results

Figure 9:
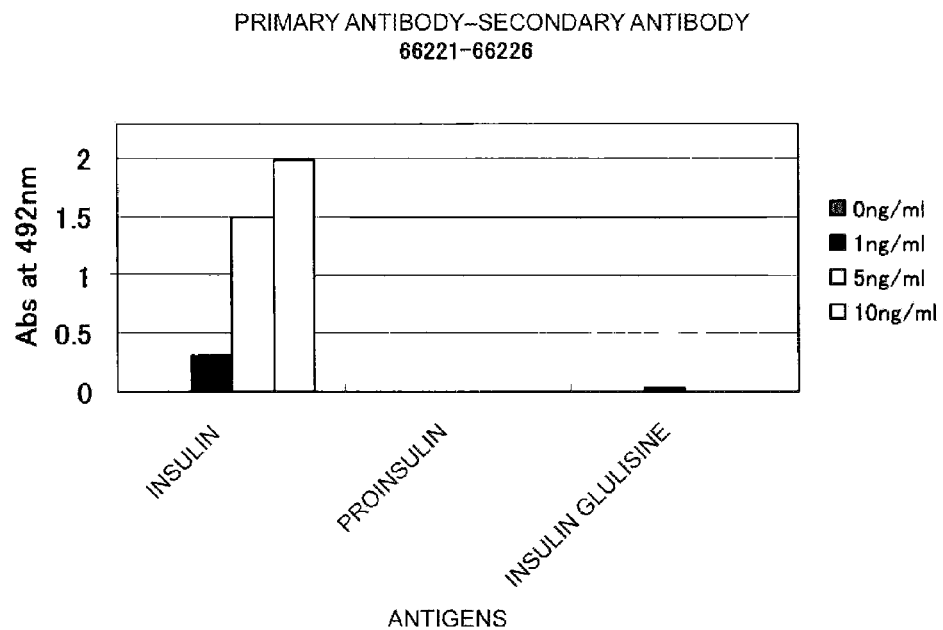
FIG. 9 is a diagram of a result of an ELISA test for examining reactivity with insulin, proinsulin, and an insulin analog formulation, insulin glulisine, using the 66221-antibody and 66226-antibody as the primary and secondary antibodies, respectively, with the primary antibody solid-phased on a plate.

Test results are depicted in Table 4 and FIG. 9.

As was the case with Example 2, when the 66221-antibody was used as the primary antibody and the 66226-antibody was used as the secondary antibody, a concentration-dependent increase in absorbance was detected for insulin while no concentration-dependent increase in absorbance was detected for proinsulin and the insulin analog formulation (insulin glulisine).

TABLE 4

| Primary antibody<br>Secondary antibody | 66221-antibody<br>Biotin-labeled 66226-antibody | | |
|---|---|---|---|
| | Antigens | | |
| Antigen concentration | Human insulin | Human proinsulin | Insulin analog formulation/ insulin glulisine |
| 0 ng/mL | 0.000 | 0.000 | 0.000 |
| 1 ng/mL | 0.316 | 0.005 | 0.031 |
| 5 ng/mL | 1.491 | 0.006 | 0.000 |
| 10 ng/mL | 1.995 | −0.013 | 0.003 |

3-2. 66226 Solid-Phase Antibody Plate Assay Results

Figure 10:
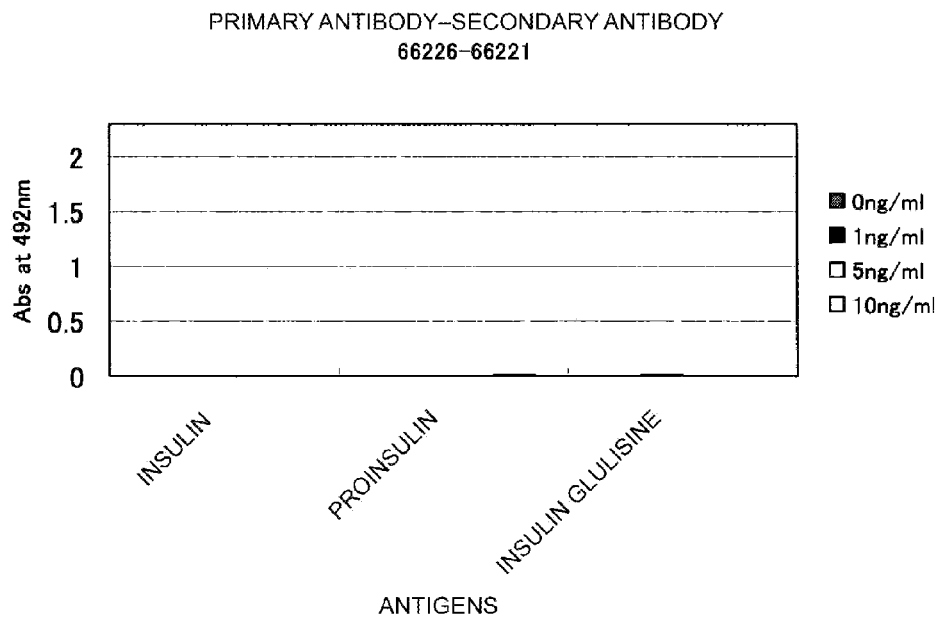
FIG. 10 is a diagram of a result of an ELISA test for examining reactivity with insulin, proinsulin, and an insulin analog formulation, insulin glulisine, using the 66226-antibody and 66221-antibody as the primary and secondary antibodies, respectively, with the primary antibody solid-phased on a plate.

Test results are depicted in Table 5 and FIG. 10.

As was the case with Example 2, when the 66226-antibody was the primary antibody and the 66221-antibody was the secondary antibody, no concentration-dependent increase in absorbance was detected for insulin, proinsulin, or the insulin analog formulation (insulin glulisine).

TABLE 5

| Primary antibody<br>Secondary antibody | 66226-antibody<br>Biotin-labeled 66221-antibody | | |
|---|---|---|---|
| | Antigens | | |
| Antigen concentration | Human insulin | Human proinsulin | Insulin analog formulation/ insulin glulisine |
| 0 ng/mL | 0.000 | 0.000 | 0.000 |
| 1 ng/mL | −0.011 | −0.002 | 0.022 |

TABLE 5-continued

| Primary antibody<br>Secondary antibody | 66226-antibody<br>Biotin-labeled 66221-antibody | | |
|---|---|---|---|
| | Antigens | | |
| Antigen concentration | Human insulin | Human proinsulin | Insulin analog formulation/ insulin glulisine |
| 5 ng/mL | −0.010 | 0.004 | 0.001 |
| 10 ng/mL | −0.010 | 0.014 | 0.001 |

4. Discussion

The above results show that no cross-reactivity is exhibited with the insulin analog formulation, insulin glulisine, when the 66221-antibody and 66226-antibody were used as the primary and secondary antibodies, respectively, and when the 66226-antibody and 66221-antibody were used as the primary and secondary antibodies, respectively.

INDUSTRIAL AVAILABILITY

With the monoclonal antibodies of the present invention, insulin can sensitively and specifically be assayed without being affected by proinsulin and insulin analogs. Since insulin secretion from the beta cells can be accurately monitored by the present invention, the present invention may also be used for visualizing a clinical condition of diabetes and is therefore very useful.

Accession Number (1) FERM BP-11233
(2) FERM BP-11234
[Reference to Deposited Biological Material]
(1) Hybridoma 66221 producing the 66221-antibody
i) Name and address of depository institution at which the biological materials were deposited.
International Patent Organism Depositary, National Institute of Advanced Industrial Science and Technology
Tsukuba Central 6, 1-1-1 Higashi, Tsukuba, Ibaraki 305-8566, Japan
ii) Date of biological material deposit in the depository institution in i).
Apr. 8, 2009 (original deposit date)
Feb. 17, 2010 (date of transfer to the Budapest Treaty from the original deposit)
iii) Accession number for the deposition assigned by the depository institution in i).
FERM BP-11233
(2) Hybridoma 66226 producing the 66226-antibody
i) Name and address of depository institution at which the biological materials were deposited.
International Patent Organism Depositary, National Institute of Advanced Industrial Science and Technology Tsukuba Central 6, 1-1-1 Higashi, Tsukuba, Ibaraki 305-8566, Japan
ii) Date of biological material deposit in the depository institution in i).
Apr. 8, 2009 (original deposit date)
Feb. 17, 2010 (date of transfer to the Budapest Treaty from the original deposit)
iii) Accession number for deposition assigned by the depository institution in i).
FERM BP-11234.

The invention claimed is:

1. An insulin assay method comprising the steps of:
   contacting a sample containing insulin with a first monoclonal antibody reagent and a second monoclonal antibody reagent, wherein
   1) the first monoclonal antibody reagent is the monoclonal antibody 66221, which is produced by a hybridoma which has a depository accession number of FERM BP-11233, and
   2) the second monoclonal antibody reagent is the monoclonal antibody 66226, which is produced by a hybridoma that has a depository accession number of FERM BP-11234, and
   detecting binding of the first monoclonal antibody reagent and the second monoclonal antibody reagent to insulin in the sample and thereby obtaining a measurement value which is dependent on the concentration of insulin in the sample.

2. The insulin assay method of claim 1, wherein the first monoclonal antibody reagent and the second monoclonal antibody reagent are immobilized to latex particles and insulin is assayed by latex immunoagglutination assay.

3. The insulin assay method of claim 1, wherein the first monoclonal antibody reagent is immobilized to a solid phase, the second monoclonal antibody reagent is labeled with a labeling material, and insulin is assayed by ELISA.

4. The insulin assay method of claim 1, wherein the first monoclonal antibody reagent is labeled with a labeling material, the second monoclonal antibody reagent is immobilized to a solid phase, and insulin is assayed by immunochromatography.

* * * * *

SEQUENCE LISTING

```
<160> NUMBER OF SEQ ID NOS: 8

<210> SEQ ID NO 1
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: Insulin A chain

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Insulin B chain

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Insulin lispro B chain

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Insulin aspart B chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

```
<210> SEQ ID NO 5
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: Insulin glargine A chain

<400> SEQUENCE: 5

Gly Ile Val Glu Gln Cys Cys Thr Ser Ile Cys Ser Leu Tyr Gln Leu
 1               5                  10                  15

Glu Asn Tyr Cys Gly
            20

<210> SEQ ID NO 6
<211> LENGTH: 32
<212> TYPE: PRT
<213> ORGANISM: Homo sapiens
<220> FEATURE:
<221> NAME/KEY: MISC_FEATURE
<222> LOCATION: (1)..(32)
<223> OTHER INFORMATION: Insulin glargine B chain

<400> SEQUENCE: 6

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

<210> SEQ ID NO 7
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: Insulin detemir B chain
<220> FEATURE:
<221> NAME/KEY: LIPID
<222> LOCATION: (29)..(29)
<223> OTHER INFORMATION: MYRISTATE

<400> SEQUENCE: 7

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys
            20                  25

<210> SEQ ID NO 8
<211> LENGTH: 30
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Insulin glulisine B chain

<400> SEQUENCE: 8

Phe Val Lys Gln His Leu Cys Gly Ser His Leu Val Glu Ala Leu Tyr
 1               5                  10                  15

Leu Val Cys Gly Glu Arg Gly Phe Phe Tyr Thr Pro Glu Thr
            20                  25                  30
```